US008067044B2

(12) United States Patent
Henry et al.

(10) Patent No.: US 8,067,044 B2
(45) Date of Patent: Nov. 29, 2011

(54) **COSMETIC COMPOSITIONS CONTAINING AN EXTRACT OF LEAVES OF THE *CASTANEA SATIVA* PLANT AND COSMETIC TREATMENTS**

(75) Inventors: Florence Henry, Villers-les-Nancy (FR); Louis Danoux, Saulzures les Nancy (FR); Gilles Pauly, Nancy (FR)

(73) Assignee: Cognis France S.A.S., Boussens (FR)

( * ) Notice: Subject to any disclaimer, the term of this patent is extended or adjusted under 35 U.S.C. 154(b) by 0 days.

(21) Appl. No.: 10/597,964

(22) PCT Filed: Feb. 4, 2005

(86) PCT No.: PCT/EP2005/001105
§ 371 (c)(1),
(2), (4) Date: Jan. 16, 2007

(87) PCT Pub. No.: WO2005/079741
PCT Pub. Date: Sep. 1, 2005

(65) Prior Publication Data
US 2007/0237847 A1    Oct. 11, 2007

(30) Foreign Application Priority Data

Feb. 13, 2004  (EP) .................................... 04290388

(51) Int. Cl.
*A61K 36/00* (2006.01)
(52) U.S. Cl. ...................................... 424/774; 424/725
(58) Field of Classification Search .................. None
See application file for complete search history.

(56) References Cited

U.S. PATENT DOCUMENTS

| | | | | |
|---|---|---|---|---|
| 3,849,548 A | * | 11/1974 | Grand | 424/70.17 |
| 5,807,543 A | * | 9/1998 | Coffindaffer et al. | 424/70.11 |
| 6,184,247 B1 | * | 2/2001 | Schneider | 514/474 |
| 6,191,083 B1 | * | 2/2001 | Brooks et al. | 510/124 |
| 6,372,842 B1 | * | 4/2002 | Grisso et al. | 524/547 |
| 6,544,499 B1 | * | 4/2003 | Glenn et al. | 424/70.1 |
| 6,630,516 B2 | * | 10/2003 | Varani et al. | 514/725 |
| 6,667,047 B2 | * | 12/2003 | Brown et al. | 424/401 |
| 2001/0024664 A1 | * | 9/2001 | Obukowicz et al. | 424/725 |
| 2006/0222619 A1 | * | 10/2006 | Perrier et al. | 424/74 |
| 2010/0098751 A1 | * | 4/2010 | Dumas et al. | 424/450 |

FOREIGN PATENT DOCUMENTS

| | | | |
|---|---|---|---|
| DE | 37 00 188 | | 7/1988 |
| FR | 2850273 | * | 7/2004 |
| FR | 2850273 A1 | | 7/2004 |
| JP | 07196526 A | | 8/1995 |
| JP | 08-217688 | * | 8/1996 |
| JP | 08217682 A | | 8/1996 |
| JP | 08217687 A | | 8/1996 |
| JP | 08217688 A | | 8/1996 |
| JP | 2002167321 A | | 6/2002 |
| JP | 2004175734 A | | 6/2004 |
| JP | 2004175767 A | | 6/2004 |
| JP | 2004323400 A | | 11/2004 |

OTHER PUBLICATIONS

Robert, P.C. Symp. Biol. Hung. 1976. vol. 16, pp. 223-227.*
Chiej, R. The MacDonald Encyclopedia of Medicinal Plants. 1984. Plant # 72 (herbal description of *Castanea sativa*) MacDonald Publishing, London, England.*
Chevallier, A. Encyclopedia of Herbal Medicine. 2nd American edition. 2000. p. 291. DK Publishing, New York, NY.*
"International Cosmetic Ingredient Dictionary and Handbook" Ninth Edition 2002, vol. 1, "*Castanea sativa*", 276 XP007911929.
"Encyclopedia of Common Natural Ingredients, Used in Food, Drugs, and Cosmetics" A. Leung & S. Foster, Second Edition, 1996, "Chestnut Leaves", 158-159 XP007911933.
"Antibacterial and allelopathic activity of extract from *Castanea sativa* leaves" A. Basile et al. Fitoterapia, 2000, 71, 5110-5116 XP007911934.
"Reedrogen und Phytopharmaka" M. Wichtl, 2002, "*Castaneae folium*" Wissenschaftliche Verlagsgesellschaft mbH, Stuttgart, pp. 122-123 XP007911935.
"Communication pursuant to Article 94(3) EPC" citing prior art Appln. No. 05707 184.7-1521 dated Mar. 2, 2010.
Oezer et al., "Quantitative determination and inhibitory effects of *Castaneda sativa* extracts containing ellargic acid on melanogenesis", Journal of Cosmetic Dermatology, 2002, vol. 1, pp. 149-169. XP002330772.
A. Hatvani, "Sweet chestnut (*Castanea sativa* Mill.) in cosmetics", Journal of Oil Soap Cosmetics, 2003, vol. 52, pp. 56-57. XP008048100.
Bundesanzeiger n° 76, Apr. 23, 1987 (unavailable).
Basile et al., "Antibacterial and allelopathic activity of extract from *Castanea sativa* leaves", Fitoterapia, 2000, vol. 71, pp. 110-116.
Wichtl, *Herbal drugs and phytopharmaceuticals: a hand book for practice on a scientific basis*, NG CRC Press, 1994, p. 566.
Wagner, *Plant drug analysis, A thin layer Chromatography atlas* (2nd edition), Springer Verlag, 1996, p. 384.
Chapman, CD rom phytochemical dictionary (unavailable), 2000.
Romussi et al., "Nebenflavonoide der Blaetter von *Castanea sativa* Mill", Ciarallo G. Pharmazie, 1981, vol. 36, p. 718.
Marsili et al., "Some constituents of the leaves of *Castanea sative*", Phytochemistry, 1972, vol. 11, pp. 2633-2634.
Jones et al., "A note on the ascorbic acid content of some trees and woody shrubs", Phytochemistry, 1984, vol. 23, pp. 2366-2367.
Die Kosmetik-Verordnung, Deutsches Institut für Körperpflege und Hygiene e.V., Appendix 6, Parts A and B, 2000.
McCord et al., "Human Keratinocytes Possess an sn-2 Acylhydrolase that is Biochemically Similar to the U937-Derived 85-kDa Phospholipase A2", Soc. for Invest.Dermatology, 1994, vol. 102, pp. 980-986.
Bouclier et al., "Prostaglandines et leucotrienes en physiologie cutanee," Bulletin d'esthetique Dermatologique et de Cosmetologie, 1986, pp. 17-22.
Deby et al., "Relation entre les acides gras essentiels et le taux des antioxydants tissulaires chez la Souris", Societe Belge de Biologie, 1970, pp. 2675-2680.

(Continued)

*Primary Examiner* — Christopher R. Tate
(74) *Attorney, Agent, or Firm* — Diehl Servilla LLC

(57) ABSTRACT

The present invention is concerned with a composition comprising an extract of the leaves of the *Castanea sativa* plant. It is furthermore directed to the use of the extract for the manufacture of a cosmetic composition and with the use of this extract for the cosmetic treatment of the human body.

23 Claims, No Drawings

OTHER PUBLICATIONS

Halliwell et al., "The Deoxyribose Method: A Simple "Test-Tube" Assay for Determination of Rate Constants for Reactions of Hydroxyl Radicals", Analytical Biochemistry, 1987, vol. 165, pp. 215-219.

Ohkuma et al., "Superoxide Dismutase in Epidermis (1)", Journ. of Dermatology, 19087, vol. 14, pp. 218-223, 1987.

Robert et al., "Vieillissement et tissu conjonctif", L'Annee Gerontologique, 1992, pp. 23-37.

* cited by examiner

COSMETIC COMPOSITIONS CONTAINING AN EXTRACT OF LEAVES OF THE *CASTANEA SATIVA* PLANT AND COSMETIC TREATMENTS

RELATED APPLICATIONS

This application is filed under 35 U.S.C. §371 claiming priority from application PCT/EP2005/001105 filed Feb. 4, 2005, which claims priority from European application EP 04290388.0 filed Feb. 13, 2004; the entire contents of each document are incorporated herein by reference.

FIELD OF THE INVENTION

The present invention is concerned with a composition comprising an extract of the leaves of the plant *Castanea sativa*. It is furthermore concerned with the use of this extract for the manufacture of a cosmetic composition and with the use of this extract for the cosmetic treatment of the human body.

BACKGROUND OF THE INVENTION

*Castanea sativa* means the plant that in detail is called *Castanea sativa* Mill. (synonyms: *Castanea vesca* Gaertn., *Castanea vulgaris* Lam.). "Mill." denotes the nomenclature system used.

*Castanea sativa* (in the following text sometimes abbreviated as *Castanea*) belongs to the family Fagaceae. Common names for *Castanea sativa* are sweet chestnut and Spanish chestnut.

The use of chestnut leaves against complaints affecting the respiratory tract, such as bronchitis, cough, and disorders affecting the legs and the circulation is known. Like other tannin-containing drugs, chestnut leaves can be used as an astringent (Bundesanzeiger n° 76, dated Apr. 23, 1987).

Antibacterial and allelopathic activity of extracts of *Castanea sativa* leaves is known (BASILE A., SORBO S., GIORDANO S., RICCIARDI L.; FERRARA S., MONTESANO R., CASTALDO COBIANCHI R., VUOTTO M. L., FERRARA L., "Antibacterial and allelopathic activity of extract from *Castanea sativa* Mill. Leaves", FITOTERAPIA, volume 71, pages 110 to 116, published in 2000). In this publication the following is disclosed: Following the extraction of *Castanea sativa* leaves with an aqueous solution of sulfuric acid (pH 3.0), the ethyl acetate soluble fraction was tested for its antibacterial and allelopathic activity. The extract was shown to have pronounced antibacterial effects against seven of the eight strains of Gram-positive and Gram-negative bacteria used (MIC in the range of 64-256 microg/ml and MBC in the range of 256-512 microg/ml) (MBC=Minimum Bactericidal Concentration, MIC=minimal inhibiting concentration). The active fraction was analysed by TLC (thin layer chromatography) and HPLC showing the presence of rutin, hesperidin, quercetin, apigenin, morin, naringin, galangin and kaempferol. Standards of the identified flavonoids were tested against the same bacterial strains. The highest activity was shown by quercetin, rutin and apigenin. The allelopathic effect was tested against *Raphanus sativus* seed germination. The extract, quercetin, rutin and apigenin caused a decrease in the percentage of seed germination and root and epicotyl growth.

The following documents of the state of the art describe the constituents that are contained in the leaves of *Castanea sativa*.

According to Wichtl et al. (Wichtl M, Bisset in Herbal drugs and phytopharmaceuticals: a hand book for practice on a scientific basis, NG CRC PRESS, 1994, page 566) the leaves of *Castanea sativa* contain ca. 9% tannins whose nature is not precisely known (both gallic and ellagic acids have been detected), flavonoids especially quercetin derivatives, triterpens e.g. ursolic acid and ca. 0.2% vitamin C.

According to Wagner et al. 1996 (Wagner H., Bladt S. in Plant drug analysis, A thin Layer Chromatography atlas (2nd edition), Springer Verlag, 1996, page 384), the main constituents of *Castanea sativa* leaves are rutin, isoquercitrin, astragalin (e.g. kaempferol-3-O-glucoside), quercetin galacturonide, O p-coumaroyl quinic acid, saponins and fructose.

Kaempferol $2^G$-coumaroylrutinoside has been isolated from *Castanea sativa* (according to "Chapman, CD rom phytochemical dictionary").

According to Basile et. al. (BASILE A., SORBO S., GIORDANO S., RICCIARDI L., FERRARA S., MONTESANO R., CASTALDO COBIANCHI R., VUOTTO M. L., FERRARA L., Antibacterial and allelopathic activity of extract from *Castanea sativa* Mill. leaves, FITOTERAPIA, volume 71, pages 110 to 116, published in 2000) after hydrolysis the main constituents of *Castanea sativa* leaves are rutin, hesperidin, quercetin, apigenin, morin, naringin, galangin and kaempferol.

According to "Duke chemical data base" (a phytochemical and ethnobotanical data base), the main constituents of *Castanea sativa* leaves are betulin (1000 ppm), caffeic acid, ellagic acid, fat (81 000 ppm), gallic acid, hamamelose, kaempferol, pectin, protein (80 000 ppm), quercetin and tannin (90 000 ppm).

According to Romussi et. al. (ROMUSSI G., MOSTIN M., Nebenflavonoide der Blätter von *Castanea sativa* Mill. 3. Mitteilung: Über Inhaltsstoffe von Cupuliferae CIARALLO G. PHARMAZIE, volume 36, page 718, 1981), the main constituents of the leaves of *Castanea sative* are narcissin (synonym: Isorhamnetin 3-beta-rutinoside) and helichrysoside (synonym Quercetin, 3-O-beta-D-(6"O-p-coumaroyl)-glucopyranoside).

According to Marsili et al. (Phytochemisty, vol. 11, pages 2633 to 2634, 1972: "Some constituents of the leaves of *Castanea sativa*") the following constituents have been identified in the leaves of *Castanea sativa*: waxes 0.1%, ursolic acid 0.2%, lupeol 0.4%, betulin 0.1%, aliphatic hydrocarbons 0.04%, fatty acids 1.58%.

According to Jones el et al. (Phytochemisty, vol. 23, pages 2666 to 2667, 1984: "A note on the ascorbic acid content of some trees and woody shrubs") the ascorbic acid content in the leaves of *Castanea sativa* is 191.3+−24.1 mg per 100 g leaves.

The problem underlying the present invention is the need for substances that can be used in cosmetic applications.

BRIEF DESCRIPTION OF THE INVENTION

Surprisingly it has been found that an extract of the leaves of the plant *Castanea sativa* is useful for cosmetic purposes.

A subject of the present invention is a composition comprising an extract of the leaves of the plant *Castanea sativa* and auxiliaries and/or additives which are common for cosmetic purposes.

DETAILED DESCRIPTION OF THE INVENTION

The extract of the leaves of the plant *Castanea sativa* is called the extract according to the present invention. The composition as defined in the previous paragraph is called the composition according to the present invention.

In one embodiment of the present invention the auxiliaries and/or additives which are common for cosmetic purposes are selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

In one embodiment of the present invention the concentration of the extract according to the present invention in the composition according to the present invention is 0.001 weight-% to 10 weight-%, preferably 0.01 weight-% to 5 weight-%, more preferably 0.1 weight-% to 3 weight-%.

In one embodiment of the present invention the extract according to the present invention is obtainable by extracting the leaves of the plant *Castanea sativa* with a solvent selected from the group consisting of water, an alcohol (preferably methanol) and mixtures thereof (preferred solvents are water, methanol and a mixture of 80% by volume methanol and 20% by volume water) so that a solution of the extract in the solvent is obtained, and removing the solvent from this solution, so that the extract is obtained.

Another subject of the present invention is the use of an extract of the leaves of the plant *Castanea sativa* or of the composition according to the present invention for the cosmetic treatment of the human body. This use is called the use according to the present invention.

In one embodiment of the present invention the use according to the present invention comprises an anti-ageing effect.

In one embodiment of the present invention the use according to the present invention comprises the protection of human skin cells against UV-radiation ("UV-cytophotoprotection").

In one embodiment of the present invention the use according to the present invention comprises an anti-inflammatory effect or an anti-itching effect or an appeasing effect or an anti-free-radicals effect or an anti-protease effect (except against matrix metalloproteases) or an anti-lipoxygenase effect.

In one embodiment of the present invention, the use according to the present invention comprises alleviating the heavy legs syndrome.

In one embodiment of the present invention the use according to the present invention comprises a whitening effect or a lightening effect.

Another subject of the present invention is the use of an extract of the leaves of the plant *Castanea sativa* for the production of a cosmetic composition, preferably for the production of a composition according to the present invention.

The cosmetic treatment of the human body can be the treatment of human skin, human hair or human skin appendices. Skin appendices means nails, sebaceous glands, sweat glands etc.

Preferably the extract of the leaves of the plant *Castanea sativa* contains polyphenols.

The extract according to the present invention has many advantages. It has many biological activities which are advantageous for its cosmetical use. Some of these advantageous properties have been described in the previous paragraphs. Further advantages are described in the experimental section.

The auxiliaries and additives which are common for cosmetic purposes can be selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

In one embodiment of the present invention the auxiliaries and additives which are common for cosmetic purposes are selected from the group consisting of surfactants, emulsifiers, fats, waxes, stabilizers, deodorants, antiperspirants, antidandruff agents and perfume oils.

The total content of auxiliaries and additives may be 1 to 50% by weight, preferably 5 to 40% by weight, based on the cosmetic and/or pharmaceutical preparations. The preparations can be prepared by customary cold or hot processes; preference is given to using the phase-inversion temperature method.

For the purposes of the invention, cosmetic preparations can mean care agents. Care agents are understood as meaning care agents for skin and hair. These care agents include, inter alia, cleansing and restorative action for skin and hair.

Application can be topical or oral in the form of tablets, dragees, capsules, juices, solutions and granules.

The compositions and cosmetic preparations according to the invention can be used for the preparation of cosmetic and/or dermopharmaceutical preparations, e. g. hair shampoos, hair lotions, foam baths, shower baths, creams, gels, lotions, alcoholic and aqueous/alcoholic solutions, emulsions, wax/fat compositions, stick preparations, powders or ointments. Furthermore, the preparations for oral application according to the invention can also be incorporated into tablets, dragees, capsules, juices, solutions and granules.

Surfactants (or Surface-active substances) that may be present are anionic, non-ionic, cationic and/or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefin sulfonates, alkyl ether sulfonates, glycerol ether sulfonates, α-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants contain polyglycol ether chains, these may have a conventional homologous distribution, but preferably have a narrowed homologous distribution. Typical examples of non-ionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucuronic acid derivatives, fatty acid N-alkylglucamides, protein hydrolysates (in particular wheat-based vegetable products), polyol fatty acid esters, sugar esters, sorbitan esters, polysorbates and amine oxides. If the non-ionic surfactants contain polyglycol ether chains, these may have a conventional homologous distribution, but preferably have a narrowed homologous distribution. Typical examples of cationic surfactants are quaternary ammonium compounds, e.g. dimethyldistearyl-ammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazolinium-betaines and sulfobetaines. Said surfactants are known compounds. With regard to structure and preparation of these substances, reference may be made to relevant review works.

Typical examples of particularly suitable mild, i.e. particularly skin-compatible surfactants are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably based on wheat proteins.

Suitable oily bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, in particular dioctyl malates, esters of linear and/or branched fatty acids with polyhydric alcohols (for example propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, for example dicaprylyl carbonates (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, for example dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, for example squalane, squalene or dialkylcyclohexanes.

Suitable emulsifiers are, for example, nonionogenic surfactants from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical;

alkyl and/or alkenyl oligoglycosides having 8 to 22 carbon atoms in the alk(en)yl radical and the ethoxylated analogs thereof;

addition products of from 1 to 15 mol of ethylene oxide onto castor oil and/or hydrogenated castor oil;

addition products of from 15 to 60 mol of ethylene oxide onto castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen® grades (TR-1, TR-2) from Goodrich;

polyalkylene glycols and glycerol carbonate.

The addition products of ethylene oxide and/or of propylene oxide onto fatty alcohols, fatty acids, alkylphenols or onto castor oil are known, commercially available products. These are homologous mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide onto glycerol are known as refatting agents for cosmetic preparations.

Alkyl and/or alkenyl oligoglycosides, their preparation and their use are known from the prior art. They can be prepared by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value that is based on a homologous distribution customary for such technical-grade products.

Typical examples of suitable partial glycerides are hydroxy stearic acid monoglyceride, hydroxy stearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linoleic acid monoglyceride, linoleic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide onto said partial glycerides.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of 1 to 30 mol, preferably 5 to 10 mol, of ethylene oxide onto said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term "zwitterionic surfactants" refers to those surface-active compounds that carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds that, apart from a $C_{8/18}$-alkyl or -acyl group in the molecule, contain at least one free amino group and at least one —COON or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyl-taurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkyl aminopropionate, cocoacyl-aminoethyl aminopropionate and $C_{12/18}$-acylsarcosine. Finally, cationic surfactants are also suitable emulsifiers, those of the ester quat type, preferably methyl-quaternized difatty acid triethanolamine ester salts, being particularly preferred.

Fats and waxes that can be used are described in the following text. Typical examples of fats are glycerides, i.e. solid or liquid vegetable or animal products which consist essentially of mixed glycerol esters of higher fatty acids, suitable waxes are inter alia natural waxes, for example candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), for example montan ester waxes, sasol waxes, hydrogenated jojoba waxes, and synthetic waxes, for example polyalkylene waxes and polyethylene glycol waxes. In addition to the fats, suitable additives are also fat-like substances, such as lecithins and phospholipids. The term lecithins is understood by the person skilled in the art as meaning those glycerophospholipids which form from fatty acids, glycerol, phosphoric acid and choline by esterification. Lecithins are thus frequently also known as phosphatidylcholines (PC). Examples of natural lecithins which may be mentioned are the cephalins, which are also referred to as phosphatidic acids and represent derivatives of 1,2-diacyl-sn-glycerol-3-phosphoric acids. By contrast, phospholipids are usually understood as meaning mono- and, preferably, diesters of phosphoric acid with glycerol (glycerophosphates), which are generally considered to be fats. In addition, sphingosines and sphingolipids are also suitable.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, for example fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying agents and thickeners that can be used are described in the following text. Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and Tyloses, carboxymethylcellulose and hydroxyethylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, for example ethoxylated fatty acid glycerides, esters of fatty acids with polyols for example pentaerythritol or trimethylolpropane, fatty alcohol ethoxylates having a narrowed homolog distribution or alkyl oligoglucosides, and electrolytes such as sodium chloride and ammonium chloride.

Superfatting agents which can be used are for example lanolin and lecithin, and polyethoxylated or acylated lanolin and lecithin derivatives, polyol fatty acid esters, monoglycerides and fatty acid alkanolamides, the latter also serving as foam stabilizers.

Stabilizers which can be used are metal salts of fatty acids, for example magnesium, aluminium and/or zinc stearate or ricinoleate.

Polymers that can be used are described in the following text. Suitable cationic polymers are, for example, cationic cellulose derivatives, for example a quaternized hydroxyethylcellulose obtainable under the name Polymer JR 400® from Amerchol, cationic starch, copolymers of diallylammonium salts and acryl amides, quaternized vinylpyrrolidone-vinylimidazole polymers, for example Luviquat® (BASF), condensation products of polyglycols and amines, quaternized collagen polypeptides, for example lauryldimonium hydroxypropyl hydrolysed collagen (Lamequat® L/Grünau), quaternized wheat polypeptides, polyethyleneimine, cationic silicone polymers, for example amodimethicones, copolymers of adipic acid and dimethylaminohydroxypropyldiethylenetriamine (Cartaretins®/Sandoz), copolymers of acrylic acid with dimethyl diallylammonium chloride (Merquat® 550/Chemviron), polyaminopolyamides and cross linked water-soluble polymers thereof, cationic chitin derivatives, for example quaternized chitosan, optionally in microcrystalline dispersion, condensation products from dihaloalkyls, for example dibromobutane with bisdialkylamines, for example bis-dimethylamino-1,3-propane, cationic guar gum, for example Jaguar® CBS, Jaguar® C-17, Jaguar® C-16 from Celanese, quaternized ammonium salt polymers, for example Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tert-butylamino-ethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

Deodorants and antimicrobial agents that can be used are described in the following text. Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against gram-positive bacteria, for example 4-hydroxybenzoic acid and its salts and esters, N-(4-chlorophenyl)-N'-(3,4-dichloro-phenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, for example n-octylsalicylamide or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", for example extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, for example civet and castoreum. Typical synthetic fragrance compounds are products of the ester, ether, aldehyde, ketone, alcohol and hydro-carbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evemyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise one or more of the following ingredients: astringent active ingredients, oil components, nonionic emulsifiers, coemulsifiers, bodying agents, auxiliaries, for example thickeners or complexing agents, and/or nonaqueous solvents, for example ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be anti-inflammatory, skin-protective or perfumed ethereal oils, synthetic skin-protective active ingredients and/or oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, for example xanthan gum, hydroxyethylcellulose, polyvinylpyrrolidone or high molecular weight polyethylene oxides.

Film formers that can be used are described in the following text. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl]-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicylic acid (or in combination with hexachlorophene), undecylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

The swelling agents for aqueous phases may be montmorillonites, clay mineral substances, Pemulen, and alkyl-modified Carbopol grades (Goodrich).

Suitable insect repellents are N,N-diethyl-m-toluamide, 1,2-pentanediol or ethyl butylacetylaminopropionate.

To improve the flow behavior, hydrotropes, for example ethanol, isopropyl alcohol, or polyols, can be used. Polyols which are suitable here preferably have 2 to 15 carbon atoms and at least two hydroxyl groups. The polyols can also contain further functional groups, in particular amino groups, or be modified with nitrogen. Typical examples are:

glycerol;
alkylene glycols, for example, ethylene glycol, diethylene glycol, propylene glycol, butylene glycol, hexylene glycol, and polyethylene glycols with an average molecular weight of from 100 to 1 000 daltons;
technical-grade oligoglycerol mixtures with a degree of self-condensation of from 1.5 to 10, for example, technical-grade diglycerol mixtures with a diglycerol content of from 40 to 50% by weight;
methylol compounds, such as trimethylolethane, trimethylolpropane, trimethylol-butane, pentaerythritol and dipentaerythritol;
lower alkyl glucosides, in particular those with 1 to 8 carbon atoms in the alkyl radical, for example methyl and butyl glucoside;
sugar alcohols with 5 to 12 carbon atoms, for example sorbitol or mannitol,
sugars with 5 to 12 carbon atoms, for example glucose or sucrose;
amino sugars, for example glucamine;
dialcohol amines, such as diethanolamine or 2-amino-1,3-propanediol.

Suitable preservatives are, for example, phenoxyethanol, formaldehyde solution, parabenes, pentanediol or sorbic acid, and the other classes of substance listed in Annex 6, Part A and B of the Cosmetics Directive.

Perfume oils which may be used are preferably mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzyl-acetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evemyl, iraldein gamma, phenylacetic acid, geranyl acetate, benzyl acetate, rose oxide, romilat, irotyl and floramat alone or in mixtures.

Dyes which can be used are the substances which are approved and suitable for cosmetic purposes. These dyes are normally used in concentrations of from 0.001 to 0.1% by weight, based on the total mixture.

EXAMPLES

Process for the Aqueous Extraction of *Castanea sativa* Leaves 0.2 kg of dried and powered powdered *Castanea sativa* leaves were introduced into a beaker containing 2 l of distilled water. The mixture was then stirred at 60° C. for an hour. The solids were removed by centrifugation (4200 rpm for 15 minutes) and filtration. The filtered solution formed a crude solution of the extract, the water was removed by spray drying and the obtained yield was 6.22% of the weight of the dried leaves. The extract thus obtained is called "aqueous extract". It was used for the experiments which are described in the following text. The extraction was carried out twice resulting in two aqueous extracts: "batch A" and "batch B".
Constituents Found in this Aqueous Extract
Gallic acid, ellagic acid, rutin, isoquercitrin, Narcissin (Isorhamnetin, 3-O-rutinoside), astragalin (kaempferol-3-O-glucoside), fructose.
Process for the Alcoholic Extraction of *Castanea sativa* Leaves (80 Volume-% Methanol+20 Volume-% Water)

0.2 kg of dried and powered *Castanea sativa* leaves were introduced into a beaker containing 2 l of methanol (80% in water). The mixture was then stirred at 60° C. for an hour. The solids were removed by filtration. Methanol was removed by evaporation. Then the solution was centrifuged (5 minutes at 4200 rpm). The solution formed a crude solution of the extract, the water was removed by freeze drying and the obtained yield was 17-20% of the weight of the dried leaves. The extract thus obtained is called "alcoholic extract". It was used for the experiments which are described in the following text. The extraction was carried out twice resulting in two alcoholic extracts: "batch A" and "batch B".

Example 1

Anti-Free Radical Activity

This Experiment is Analogous to an Experiment Described in WO 02/080949

1.1 Background: Free radicals (FR) are reactive chemical species. FR can originate from unsaturated lipids, certain amino-acids and above all from oxygen during spontaneous biological mechanisms such as the respiratory chain in mitochondria, or during natural biological processes such as inflammation. Oxidative stress like UV or chemical pollutants induce also the rise of the concentration of free radicals which provokes damages on all cellular and tissue constituents (lipids, proteins, sugars and nucleic bases) of living organisms. Indeed the FR toxicity is strongly enhanced by oxygen level and constitutes a key process in ageing, in the appearance of serious diseases such as cancers, diabetes etc.

1.2 Methods and principle of this experiment: The anti-free radical (anti-FR) activity has been evaluated by chemical tests for the evaluation of the potential to scavenge free radicals R (DPPH test) and hydroxyl radicals HO. The anti-FR activity has been evaluated also by biochemical tests to address the potential for scavenging of a kind of reactive oxygen species (ROS), the so called super oxide anion ($O_2$). The $O_2$ originates mainly from xanthine oxydase and lipoxygenase activities. Xanthine oxydase (XOD) is an enzyme activated during oxidative stress, this enzyme catalyses the $O_2$ release along the degradation of hypoxanthin (HX) which has been overproduced by a disruption of energetic cell metabolism. Then $O_z$ dismutates either spontaneously or by superoxyde dismutase (SOD) activity, into hydrogen peroxide ($H_2O_2$), which constitutes a source of HO following the Fenton's reaction lipoxygenase activity, displayed by leukocytes, produces also $O_2$ along the leukotriens synthesis from arachidonic acid released during inflammatory process (Mac Cord M, Chabot Fletcher M, Breton J, Marshall La, Human keratinocytes possess an sn-2 acylhydrolase that is biochemically similar to the U937-derived 85-kDa phospholipase A2, Journal of Investigative Dermatology, 1994, n 102, pages 980 to 986 and Bouclier M, Hensby C N, Prostaglandines et leucotriènes en physiologie cutanée, Bulletin d' esthétique Dermatologique et de Cosmétologie, 1986, pages 17 to 22).
1.3.1 Anti-DPPH Test:
Principle: DPPH (diphenylpicryl-hydrazyl) is a stable free radical which forms a purple solution. The purple solution of DPPH° has a whitening effect due to components that act as radical-scavengers. The reaction is evaluated by recording the optical density (OD) at 513 nm (DEBY C:C: Relation entre les acides gras essentiels et le taux des antioxydants tissulaires chez la souris: SOCIETE BELGE DE BIOLOGIE, séance du 19 decembre 1970 (year of publication), pages 2675 to 2680).
Results (in % of inhibition/control, average of 2 assays):

| concentration of the tested product (vitamin C, aqueous or alcoholic extract) in % (w/v) | Vitamin C | aqueous extract, batch A | aqueous extract, batch B | alcoholic extract, batch A | alcoholic extract, batch B |
| --- | --- | --- | --- | --- | --- |
| control | 0 | 0 | 0 | 0 | 0 |
| 0.0003 | 19 | — | — | — | — |
| 0.001 | 58 | 31 | 23 | 29 | 35 |
| 0.003 | 74 | 69 | 64 | 81 | 87 |

-continued

| concentration of the tested product (vitamin C, aqueous or alcoholic extract) in % (w/v) | Vitamin C | aqueous extract, batch A | aqueous extract, batch B | alcoholic extract, batch A | alcoholic extract, batch B |
|---|---|---|---|---|---|
| 0.01 | 68 | 89 | 89 | 90 | 89 |
| IC50 | ~0.001% | ~0.002% | ~0.002% | ~0.002% | ~0.002% |

"% (w/v)" means % weight by volume (1 g in 100 ml is 1% (w/v))
"~" means approximately
IC50 is the concentration that inhibits 50%

The results are expressed in percent inhibition of DPPH radical against control. The aim of this test is to show an anti-free radical activity.

1.3.2 Anti-HO— Test with Deoxyribose (Fenton's Reaction):

Principle: The hydroxyl radical HO— (formed by $H_2O_2$ in presence of Fe++ with EDTA) oxidises deoxyribose (a component of DNA), then a pink compound is formed by condensation of thiobarbituric acid with oxidised form of deoxyribose. The optical density at 532 nm corresponds to the level of oxidised deoxyribose. An anti-free radical substance reacts with these radicals HO— and reduces the formation of this pink compound. This reaction is also carried out without EDTA in order to determine the capacity of ingredient to form an inactive complex with a ferrous ion (Halliwell B, Gutteridge J M C, Aruoma O I, The deoxyribose method: a simple "Test-Tube" assay for determination of rate constants for reactions of hydroxyl radicals, Analytical Biochemistry, 1987, n° 165, p 215-219).

Results (in % of inhibition/control, average of 2 assays):
Reaction with EDTA:

| concentration of the tested product (mannitol, aqueous or alcoholic extract) in % (w/v) | mannitol | aqueous extract, batch A | aqueous extract, batch B | alcoholic extract, batch A | alcoholic extract, batch B |
|---|---|---|---|---|---|
| control | 0 | 0 | 0 | 0 | 0 |
| 0.06 | 25 | — | — | — | — |
| 0.6 | 68 | — | — | — | — |
| 0.03 | — | 29 | 25 | 30 | 21 |
| 0.1 | — | 59 | 65 | 50 | 56 |
| IC50 | ~0.3% | ~0.1% | ~0.1% | 0.1% | ~0.1% |

The results are expressed in percent of inhibition of HO— radical against control. The aim of this test is to show an anti-free radical activity.

Reaction Without EDTA:

| concentration of the tested product (o-phenanthroline, aqueous or alcoholic extract) in % (w/v) | o-phenanthroline | aqueous extract, batch A | aqueous extract, batch B | alcoholic extract, batch A | alcoholic extract, batch B |
|---|---|---|---|---|---|
| control | 0 | 0 | 0 | 0 | 0 |
| 0.02 | 42 | — | — | — | — |
| 0.06 | 71 | — | — | — | — |
| 0.003 | — | 38 | 22 | 49 | 25 |
| 0.01 | — | 49 | 48 | 60 | 71 |
| 0.03 | — | 62 | 67 | 70 | 77 |
| IC50 | ~0.03% | 0.01% | 0.01% | 0.003% | 0.005% |

The results are expressed in percent of inhibition of HO— radical against control. The aim of this test is to show an anti-free radical activity.

1.4 Biochemical Tests for Superoxydes Anions 1.41 Inhibition Test on Xanthine Oxidase Xanthine oxydase is an enzyme induced during oxidative stress: it catabolises the puric bases (adenine, guanine) in uric acid and superoxide anions $O_2$— dismutates spontaneously (or by the action of SOD=superoxyde dismutase) in $H_2O_2$ and $O_2$.

The superoxidea anion $O_2$— can be revealed by NBT (NBT=Nitroblue tetrazolium) by recording the optical density at 540 nm (OHKUMA N et al.: Superoxyde dismutase in epidermis. J. of Invest. Dermatol., 1987, n 14, pages 218 to 223). A substance with an anti-free-radical-activity absorbs or destroys the $O_2$— anion and thereby it reduces the optical density.

Results, expressed in % of inhibition (average of 2 tests):

| concentration of the tested product (SOD, aqueous or alcoholic extract) in % (w/v) | SOD | aqueous extract, batch A | aqueous extract, batch B | alcoholic extract, batch A | alcoholic extract, batch B |
|---|---|---|---|---|---|
| control | 0 | 0 | 0 | 0 | 0 |
| 0.5 U/ml | 18 | — | — | — | — |
| 5 U/ml | 50 | — | — | — | — |
| 50 U/ml | 95 | — | — | — | — |
| 0.003 | — | 38 | 25 | 45 | 41 |
| 0.01 | — | 70 | 54 | 77 | 73 |
| 0.03 | — | 90 | 80 | 92 | 91 |
| IC50 | 5 U/ml | 0.006% | 0.004% | 0.003% | 0.005% |

The results are expressed in percent of inhibition of $O_2$—radical against control. The aim of this test is to show an anti-free radical activity.

As to the meaning of U/ml: for an enzyme, the dose is expressed in Units/ml for unity. In the other cases, it is not enzymes.

1.4.2 Inhibition Test on Lipoxygenase

Lipoxygenase was incubated with a specific substrate (unsaturated fatty acid) and the ingredient to be tested. Then the rate of released superoxide anions was evaluated by a luminescent probe (luminol). Caffeic acid was tested as reference ingredient.

Results, expressed as % of inhibition (average of 2 tests):

| concentration of the tested product (caffeic acid, aqueous or alcoholic extract) in % (w/v) | caffeic acid | aqueous extract, batch A | aqueous extract, batch B | alcoholic extract, batch A | alcoholic extract, batch B |
|---|---|---|---|---|---|
| control | 0 | 0 | 0 | 0 | 0 |
| 0.00002 | 18 | — | — | — | — |
| 0.0002 | 53 | — | — | — | — |
| 0.003 | — | 20 | 19 | 27 | 7 |
| 0.01 | — | 57 | 40 | 49 | 38 |
| 0.03 | — | 93 | 83 | 85 | 84 |
| IC50 | 0.0002% | 0.003% | 0.005% | 0.003% | 0.005% |

Comments on the Results of Example 1:
Stabilization of free radicals: *Castanea* extracts have shown a good potential to stabilize the free radicals (almost as high as the reference ascorbic acid).
Stabilization of hydroxyl radicals: *Castanea* extracts have shown a good potential to stabilize the hydroxyl radicals (higher than the references mannitol and o-phenanthroline). This activity is stronger without EDTA, which means that these extracts present a good potential to form stable complexes with ferrous ions.
Scavenging of superoxide anions: *Castanea* extracts have shown a good potential to scavenge superoxide anions generated by xanthine oxidase and lipoxygenase. Therefore *Castanea* extracts have shown a good potential to inhibit lipoxygenase (but less elevated than the reference caffeic acid).

Example 2

Inhibition of UVA Effect on Human Fibroblasts

This Experiment is Analogous to an Experiment Described in the European Patent Application No. 03292802.0

Aim of the experiment: Determination of the potential of the tested ingredient to reduce negative effects of UV-A radiation on the survival rate of human fibroblasts.

Protocol of the Experiment:
Seeding of human fibroblasts in a growth medium
Incubation for 3 days at 37° C., $CO_2$=5% (atmosphere: 5% carbon dioxide in air)
Exchange of the growth medium by a medium with a range of concentration of ingredients to be tested
Incubation for 2 days at 37° C., $CO_2$=5%
Exchange of the medium with ingredients by a balanced salt solution and UV-A irradiation (20 J/cm$^2$)
Recording of released MDA levels by spectro-fluorimetry. (MDA (malonaldialdehyde) is a product of oxidative degradation of lipids from cell membranes)

Results in % against control (average of 2 assays in triplicat):

| | Dose (% w/v) | Rate of released MDA |
|---|---|---|
| Control | 0 | 0 |
| UV-A 20 J/cm2 | 0 | 100 |
| Vitamin E + UV-A | 0.0003 | 7 |
| Aqueous extract, batch B + UV-A | 0.001 | 101 |
| | 0.003 | 23 |
| alcoholic extract, batch B + UV-A | 0.001 | 62 |
| | 0.003 | 38 |

UV-A irradiation has induced a strong release of MDA in human fibroblasts. Vitamin E has strongly decreased the rate of released MDA from UV-A irradiated fibroblasts. *Castanea* extracts have distinctly lowered the rate of released MDA from UVA irradiated fibroblasts.

Example 3

Inhibition of Proteases

This Experiment is Analogous to an Experiment Described in the European Patent Application No. 03292668.5

3.1 Inhibition of Elastase

Elastase is a protease which is secreted either from stressed or aged human dermal fibroblasts, or from polymorphonuclear neutrophil granulocytes during inflammation. This protease is an enzyme which catalyzes the destruction of the main dermal proteins, for example proteoglycans, elastin and collagen fibers and therefore induces the intrinsic aging as well as the photo-aging of human skin (ROBERT L, LABAT ROBERT J: Vieillissement et tissu conjonctif. Année Gérontologique, 1992, pages 23 to 37). This leads to a loss of elasticity of the skin, and to the formation of wrinkles, and to a dry skin.

The test was carried out with an elastase from pancreas on elastin labeled with Congo red. The time of incubation has been 30 minutes at room temperature and optical density of released Congo red was recorded after centrifugation at 520 nm. The results are shown in the following table in % of inhibition compared to control (=0%).

Elastase inhibition in tube vitro (in % of inhibition compared to control (=0%), average of 2 assays):

| concentration of the tested product in % (w/v) | aqueous extract, batch A | aqueous extract, batch B | alcoholic extract, batch A | alcoholic extract, batch B |
|---|---|---|---|---|
| control | 0 | 0 | 0 | 0 |
| 0.3 | 30 | 33 | 23 | 0 |

Nota Bene: reference ingredient for the assay with elastase=alpha1-anti-trypsine, IC50=0,026%

*Castanea* extracts have inhibited elastase activity in vitro, and could be used to fight against skin ageing and skin photo-ageing.

Example 4

Inhibition of Melanin Synthesis

This Experiment is Analogous to an Experiment Described in the European Patent Application No. 03292735.2

Aim of the experiment: to evaluate the potential of compounds to lower the melanin synthesis; the compounds have been tested on cell culture of melanocytes called B16.
Protocol of Efficacy Test on B16 Melanocytes:
Seeding of melanocytes in growth medium
Incubation for 3 days at 37° C., $CO_2$=5% (atmosphere: 5% carbon dioxide in air)
Exchange of the growth medium by a medium with a range of concentration of ingredients to be tested
Incubation for 3 days at 37° C., $CO_2$=5% (atmosphere: 5% carbon dioxide in air)
Recording of Cellular levels of protein by Bradford's method
Recording of melanin by a spectrophotometric method (OD at 475 nm)

Results in % against control (average of 2 assays in triplicat):

| | Dose (% w/v) | Rate of cellular proteins | Rate of melanin |
|---|---|---|---|
| control | 0 | 100 | 100 |
| kojic acid | 0.03 | 109 | 32 |
| arbutin | 0.2 | 91 | 64 |
| aqueous extract, batch A | 0.003 | 112 | 62 |
| | 0.01 | 115 | 68 |
| aqueous extract, batch B | 0.003 | 107 | 62 |
| | 0.01 | 80 | 56 |
| alcoholic extract, batch A | 0.003 | 104 | 88 |
| | 0.01 | 113 | 80 |
| alcoholic extract, batch B | 0.003 | 109 | 76 |
| | 0.01 | 103 | 65 |

Kojic acid and arbutin have strongly decreased the rate of released melanin from treated B16 melanocytes. *Castanea* extracts have distinctly lowered the rate of released melanin.

We claim:

1. A method for treating aged human skin of a subject in need thereof comprising topically applying to the aged human skin a dermopharmaceutical composition comprising:
   (a) an extract of leaves of a *Castanea sativa* plant; and
   (b) at least one cosmetic and/or dermopharmaceutical auxiliary and/or additive adapted for topical treatment of human skin selected from the group consisting of oil bodies, surfactants, emulsifiers, fats, waxes, pearlescent waxes, bodying agents, thickeners, superfatting agents, stabilizers, polymers, silicone compounds, lecithins, phospholipids, active ingredients produced by living organisms or biological processes, deodorants, antimicrobial agents, antiperspirants, film formers, antidandruff agents, swelling agents, insect repellents, hydrotropes, solubilizers, preservatives, perfume oils and dyes, in an amount effective to provide an anti-ageing effect.

2. The method of claim 1, wherein the treatment provides for the protection of human skin cells against UV-radiation.

3. The method of claim 1, wherein said treatment of aged human skin provides at least one anti-ageing effect selected from the group consisting of an anti-free-radical effect and an anti-protease effect, with the proviso that the anti-ageing effect is not an anti-matrix-metalloprotease-effect or an anti-lipoxygenase effect.

4. The method of claim 3 wherein the anti-protease effect is inhibiting the secretion of elastase present as a result of a process which produced the aged human skin.

5. The method of claim 3 wherein the anti-free radical effect is stabilizing or scavenging free radicals present as a result of a process which produced the aged human skin.

6. The method of claim 1, wherein said treatment of aged human skin provides an anti-ageing effect selected from the group consisting of a whitening effect and a lightening effect.

7. The method of claim 1, wherein the amount of the *Castanea sativa* extract in said composition is 0.001 wt % to 10 wt % based on the composition.

8. The method of claim 1, wherein, the amount of the *Castanea sativa* extract in said composition is 0.1 wt % to 3 wt % based on the composition.

9. The method of claim 1, wherein said extract is obtained by a method comprising the steps of:
(a) extracting the leaves of the *Castanea sativa* plant with a solvent selected from the group consisting of water, an alcohol and mixtures thereof, to form an extract; and
(b) removing the solvent from said extract.

10. The method of claim 7, wherein said extract is obtained by a method comprising the steps of:
(a) extracting the leaves of the *Castanea sativa* plant with a solvent selected from the group consisting of water, an alcohol and mixtures thereof, to form an extract; and
(b) removing said solvent from said extract.

11. The method of claim 1, wherein component (b) comprises a thickener.

12. The method of claim 1, wherein said thickener comprises a polysaccharide.

13. The method of claim 7, wherein component (b) comprises a thickener.

14. The method of claim 13, wherein said thickener comprises a polysaccharide.

15. The method of claim 1 wherein the dermopharmaceutical composition is topically applied to skin showing signs of ageing.

16. A method for treating aged human skin of a subject in need thereof comprising topically applying to the aged human skin a dermopharmaceutical composition, said composition consisting of:
(a) an extract of leaves of a *Castanea sativa* plant; and
(b) one or more thickeners;
in an amount effective to provide an anti-ageing effect.

17. The method of claim 16, wherein the amount of the *Castanea sativa* extract in said composition is 0.001 wt % to 10 wt % based on the composition.

18. The method of claim 16, wherein said thickeners are selected from the group consisting of polysaccharides.

19. The method of claim 17, wherein said thickeners are selected from the group consisting of polysaccharides.

20. A method for treatment of aged human skin comprising topically applying to the aged human skin dermopharmaceutical composition, said composition consisting of:
(a) an extract of leaves of a *Castanea sativa* plant;
(b) one or more thickeners; and
(c) water;
in an amount effective to inhibit the secretion of elastase present or to stabilize or scavenge free radicals present as a result of a process which produced the aged human skin.

21. The method of claim 20, wherein the amount of the *Castanea sativa* extract in said composition is 0.001 wt % to 10 wt % based on the composition.

22. The method of claim 20, wherein said thickeners are selected from the group consisting of polysaccharides.

23. The method of claim 21, wherein said thickeners are selected from the group consisting of polysaccharides.

* * * * *

UNITED STATES PATENT AND TRADEMARK OFFICE
CERTIFICATE OF CORRECTION

PATENT NO. : 8,067,044 B2
APPLICATION NO. : 10/597964
DATED : November 29, 2011
INVENTOR(S) : Florence Henry et al.

Page 1 of 1

It is certified that error appears in the above-identified patent and that said Letters Patent is hereby corrected as shown below:

Claim 12, Column 21, line 15, change the dependency from "claim 1" to -- claim 11 --.

Claim 20, Column 22, lines 8-9, change "treatment of aged human skin" to -- treating aged human skin in need thereof --.

Signed and Sealed this
Third Day of April, 2012

David J. Kappos
*Director of the United States Patent and Trademark Office*